US00PP09385P

United States Patent [19]

Zerr

[11] Patent Number: Plant 9,385

[45] Date of Patent: Nov. 28, 1995

[54] POINSETTIA PLANT NAMED 'FISFLIRT'

[75] Inventor: Katharina Zerr, Simmern, Germany

[73] Assignee: Florfis AG, Binningen, Switzerland

[21] Appl. No.: 328,054

[22] Filed: Oct. 24, 1994

[30] Foreign Application Priority Data

Dec. 29, 1993 [DE] Germany ..... EUP 146

[51] Int. Cl.[6] ..... A01H 5/00

[52] U.S. Cl. ..... Plt./86.3

[58] Field of Search ..... Plt./86.3

[56] References Cited

U.S. PATENT DOCUMENTS

P.P. 5,492 6/1985 Gutbier ..... Plt./86.4

P.P. 8,259 6/1993 Jacobsen ..... Plt./86.4

*Primary Examiner*—James R. Feyrer

*Attorney, Agent, or Firm*—Foley & Lardner

[57] ABSTRACT

A distinct cultivar of poinsettia plant named Fisflirt, characterized by the combined traits of salmon pink bract color, medium and well branched plant habit, medium green foliage, medium early flowering response, and well-developed and well-colored bracts at the time when cyathias open.

1 Drawing Sheet

Fisflirt is a product of a mutation induction program carried out by the inventor in Hillscheid, Germany in 1991. The primary objective of the induction program was to expand the bract color ranges of Peterstar, disclosed in U.S. Plant Pat. No. 8,259 and characterized by its bright red bract color, medium green foliage, comparatively compact plant habit, medium early response in autumn, and good branching ability.

The irradiation program resulting in the new cultivar comprised exposing rooted cuttings of the parent cultivar to an X-ray source of 30 Gy in Ahrensburg, Germany under the supervision of the inventor Katharina Zerr. The irradiated plants were grown out in a greenhouse in Hillscheid, Germany and were asexually propagated by taking cuttings. These cuttings were grown outdoors near Galdar, Gran Canaria, Spain, under the supervision of the inventor. Parts of plants showing mutation were out from the remainder of the plants by the inventor and planted as cuttings. The plants grown from these cuttings were identified by number and selections were made by the inventor begining in autumn 1991.

The new cultivar evolved from a basal branch of an irradiated plant having a ring of uniform pink bracts. The plant was designated No. 70 and was grown out and propagated several times by cuttings by the inventor in Hillscheid, Germany in order to obtain a plant with stable and uniform characteristics.

Horticultural examination of the new cultivar initiated in 1992 and continuing thereafter has demonstrated that the combination of characteristics as herein disclosed for Fisflirt are firmly fixed and are retained through successive generations of asexual reproduction.

The following traits have been repeatedly observed and are determined to be basic characteristics of Fisflirt which in combination distinguish this poinsettia as a new and distinct cultivar:

1. Uniform salmon pink bract.
2. Well-developed and well-colored bracts at the time when cyathias open.
3. Medium tall and well branched plant habit.
4. Medium green foliage.
5. Medium early flowering response.

Fisflirt has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commercial practice.

Of the many commercial cultivars known to the inventor, the most similar in comparison to Fisflirt are the parent cultivar Peterstar and the cultivars Dorothea and Beckmanns Altrosa. When compared to Peterstar, Fisflirt has a salmon pink rather than bright red bract color, a stronger growth habit, and relatively flat bracts which have a comparatively smooth surface. In comparison to Dorothea, Fisflirt has a more intense pink bract color at the time cyathias open, bracts are better developed, and Fisflirt has a more compact plant habit. When compared to Beckmanns Altrosa, disclosed in a pending application, Fisflirt has a lighter pink bract color, a taller plant habit, and darker, more yellow-green foliage. Fisflirt differs from grandparent cultivar Angelika in several respects, including its salmon pink bract color, compared to the bright red bract color of Angelika.

The accompanying color photographic drawing shows typical inflorescence and foliage of Fisflirt, with colors being as true as possible with illustrations of this type. In the photograph, a typical mature potted plant of Fisflirt appears on the left and a mature potted plant of comparison cultivar Beckmanns Altrosa appears on the right.

In the following description, color references are made to The Royal Horticultural Society Colour Chart. The color values were determined indoors in a north light. The plants described were grown in Hillscheid, Germany (latitude 50° N). They were planted as rooted cuttings into 14 cm pots in early August, potted in late–August and pinched 10 days later. Plants were lighted (long day conditions) from mid-September. From October 1, the plants were grown in a greenhouse under natural short day conditions at 18° C. night temperature and 18° to 24° C. day temperature. Observations and measurements were taken at the beginning of flowering when three (3) cyathias were open.

Classification:

*Botanical.*—*Euphorbia pulcherrima.*

*Commercial.*—Poinsettia, cv. Fisflirt.

Parentage: Induced mutation of Peterstar.

Plant description:

*Form.*—Broad, bushy, 10–12 branches.

*Growth habit.*—Medium height: 40 cm.

*Rooting.*—Fast less than 20 days.

Blooming season.—From early December (about 9–10 weeks of response time).

*Blooming habit.*—Saleable from early December, when 3–6 bracts are fully colored.

*Foliage.—Size: Leaf is approximately* 13–14 cm in length; petiole is 7.5 cm in length. Internodes: 25–30 mm. Color: New Foliage: Upper surface, between 143A and 144A; under surface 144A. Old Foliage: Upper surface, 147A to 137A; under surface 147B. Leaf Petiole: Light green. Shape: Broad, elliptical with very weak lobes. Texture: Upper side, weak rugosity; lower side, weak veins. Edge of margin: Entire. Disease resistance: No disease problems have been observed to date .

Flowering description:

*Cyathias.*—Borne: In a narrow cluster. Quantity: 20–24. Retention: Good.

*Bracts.*—Ovate, with comparatively smooth surface; largest colored bract with petiole is 19 cm long.

*Color.*—Pink 52C-D.

*Aspect.*—Bracts are borne horizontally and form a large, flat involucre.

Reproductive organs:

*Glands, nectar cups.*—Orange-yellow.

*Stamens.*—Light brown, hardly any fertile stamens.

*Pollen.*—No pollen.

*Styles.*—White, 6-lobed stigma with pink stripes.

*Ovaries.*—Triangular, 3-celled, 3 ovules.

I claim:

1. A new and distinct poinsettia plant named Fisflirt, as illustrated and described.

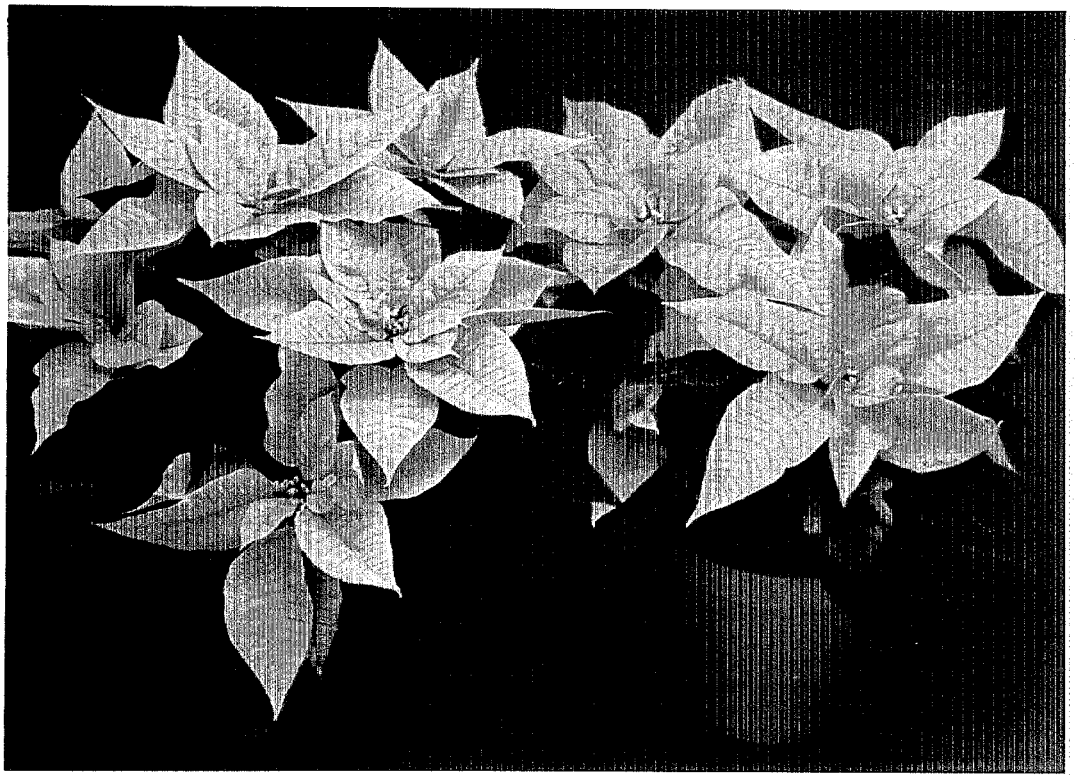

* * * * *